United States Patent
Koseoglu et al.

(10) Patent No.: US 11,370,973 B2
(45) Date of Patent: Jun. 28, 2022

(54) PROCESSES AND SYSTEMS FOR PRODUCING ONE OR MORE OF BENZENE, TOLUENE, OR MIXED XYLENES

(71) Applicant: Saudi Arabian Oil Company, Dhahran (SA)

(72) Inventors: Omer Refa Koseoglu, Dhahran (SA); Robert Peter Hodgkins, Dhahran (SA); Frederick M. Adam, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 59 days.

(21) Appl. No.: 16/925,851

(22) Filed: Jul. 10, 2020

(65) Prior Publication Data

US 2022/0009856 A1 Jan. 13, 2022

(51) Int. Cl.
*C10G 1/00* (2006.01)
*C07C 4/26* (2006.01)
(Continued)

(52) U.S. Cl.
CPC .............. *C10G 1/002* (2013.01); *B01D 3/06* (2013.01); *B01J 8/0278* (2013.01); *B01J 23/881* (2013.01); *B01J 23/882* (2013.01); *B01J 23/883* (2013.01); *B01J 23/888* (2013.01); *C07C 4/22* (2013.01); *C07C 4/26* (2013.01); *C10G 1/10* (2013.01); *C10G 11/05* (2013.01);
(Continued)

(58) Field of Classification Search
None
See application file for complete search history.

(56) References Cited

U.S. PATENT DOCUMENTS

| 2,885,452 A | 5/1959 | Schmerling et al. |
| 3,373,217 A | 3/1968 | Engelbrecht et al. |

(Continued)

FOREIGN PATENT DOCUMENTS

CN 203620613 U * 6/2014

OTHER PUBLICATIONS

ECHA "Shale Oils, heavy" pp. 1-7. Retrieved May 7, 2021 (Year: 2021).*

(Continued)

*Primary Examiner* — Philip Y Louie
*Assistant Examiner* — Alyssa L Cepluch
(74) *Attorney, Agent, or Firm* — Dinsmore & Shohl LLP (57) ABSTRACT

A process for producing one or more of benzene, toluene, or mixed xylenes may include combining one or more aromatic feed chemicals, one or more aromatic-based polymers, hydrodearylation catalyst, and hydrogen in a hydrodearylation unit to form a chemical product. The process may also include passing the chemical product out of the hydrodearylation unit, where the chemical product comprises one or more of benzene, toluene, and mixed xylenes. Additionally, a system for producing one or more of benzene, toluene, or mixed xylenes may include a mixing unit and a hydrodearylation unit. An aromatic feed stream and an aromatic-based polymer stream may be in fluid communication with a mixing unit. A mixing unit effluent stream may be in fluid communication between the mixing unit and the hydrodearylation unit. A chemical product stream may be in fluid communication with the hydrodearylation unit.

20 Claims, 4 Drawing Sheets

(51) Int. Cl.

| | | |
|---|---|---|
| *B01D 3/06* | (2006.01) | |
| *B01J 8/02* | (2006.01) | |
| *B01J 23/881* | (2006.01) | |
| *B01J 23/882* | (2006.01) | |
| *B01J 23/883* | (2006.01) | |
| *B01J 23/888* | (2006.01) | |
| *C07C 4/22* | (2006.01) | |
| *C10G 1/10* | (2006.01) | |
| *C10G 11/05* | (2006.01) | |

(52) U.S. Cl.
CPC ............ *B01J 2208/00823* (2013.01); *C10G 2300/1003* (2013.01); *C10G 2300/1096* (2013.01); *C10G 2300/301* (2013.01); *C10G 2300/308* (2013.01); *C10G 2300/4018* (2013.01); *C10G 2400/30* (2013.01)

(56) References Cited

U.S. PATENT DOCUMENTS

| | | | | |
|---|---|---|---|---|
| 3,591,651 | A * | 7/1971 | Carr | C07C 15/04 585/319 |
| 3,726,789 | A * | 4/1973 | Kovach | C07C 15/02 208/80 |
| 3,996,305 | A | 12/1976 | Berger | |
| 4,041,091 | A | 8/1977 | Henry | |
| 4,317,712 | A * | 3/1982 | Farcasiu | B01J 27/10 208/46 |
| 4,670,618 | A * | 6/1987 | Bellinger | C07C 15/08 585/478 |
| 5,079,385 | A * | 1/1992 | Wu | C07C 4/00 585/241 |
| 5,583,021 | A | 12/1996 | Dougherty et al. | |
| 7,810,642 | B2 | 10/2010 | Cheng et al. | |
| 8,658,391 | B2 | 2/2014 | Edelson | |
| 9,200,207 | B2 | 12/2015 | Huang et al. | |
| 9,434,894 | B2 | 9/2016 | Mehlberg et al. | |
| 9,775,889 | B2 | 10/2017 | Keller et al. | |
| 9,833,498 | B2 | 12/2017 | Keller et al. | |
| 10,053,401 | B1 | 8/2018 | Beadle et al. | |
| 10,093,873 | B2 | 10/2018 | Koseoglu et al. | |
| 10,208,259 | B2 | 2/2019 | Buchbinder et al. | |
| 10,294,172 | B2 | 5/2019 | Beadle et al. | |
| 10,508,066 | B2 | 12/2019 | Koseoglu et al. | |
| 10,759,723 | B2 | 9/2020 | Koseoglu et al. | |
| 2014/0027344 | A1 | 1/2014 | Harris et al. | |
| 2016/0229959 | A1 | 8/2016 | Li et al. | |
| 2018/0066197 | A1 * | 3/2018 | Koseoglu | C10G 69/00 |
| 2018/0216009 | A1 * | 8/2018 | Narayanaswamy | C10G 1/10 |
| 2018/0230070 | A1 | 8/2018 | Beadle et al. | |
| 2020/0062675 | A1 | 2/2020 | Koseoglu et al. | |

OTHER PUBLICATIONS

Machine translation CN 203620613. Accessed Jan. 14, 2022 (Year: 2022).*

ECHA Registration Dossier—Kerosine (petroleum). Accessed Jan. 14, 2022 (Year: 2022).*

Agency for Toxic Substances and Disease Registry (ATSDR). 1995. Toxicological profile for automotive gasoline. Chapter 3. Chemical and Physical Information https://wwwn.cdc.gov/TSP/ToxProfiles/ToxProfiles.aspx?id=468&tid=83 (Year: 1995).*

Smith, Robin "Chapter 13: Reaction, Separation and Recycle Systems for Continuous Processes" Chemical Process Design and Integration. Wiley 2005. (Year: 2005).*

International Search Report and Written Opinion dated Apr. 9, 2021 pertaining to International application No. PCT/US2021/012461 filed Jan. 7, 2021, 14 pgs.

* cited by examiner

PROCESSES AND SYSTEMS FOR PRODUCING ONE OR MORE OF BENZENE, TOLUENE, OR MIXED XYLENES

BACKGROUND

Field

The present disclosure relates generally to chemical processing and, more specifically, to the production of benzene, toluene, and/or mixed xylenes from streams comprising aromatics.

Technical Background

Aromatics compounds such as benzene, toluene, and xylenes (BTX) are basic intermediates for a significant portion of the petrochemical industry. They are usually obtained as byproducts of crude oil refining. For example, BTX may be recovered from naphtha streams by reforming and further processing, such as in an aromatics complex. With the ever growing demand for BTX, refineries look increasingly to the petrochemicals market to boost their revenues by taking advantage of economic opportunities that arise from the relatively high value of BTX as compared with other hydrocarbon products.

BRIEF SUMMARY

In many aromatic complexes, heavy aromatics (such as $C_9+$ aromatics) are purged from the system as relatively low value products. However, hydrodearylation of such heavy aromatics can improve BTX yields. It has been discovered that mixing aromatic-based polymers with the heavy aromatics (referred to sometimes herein as "aromatic feed chemicals") may improve the hydrodearylation conversion rate of heavy aromatics and/or aromatic-based polymers to BTX. Additionally, such aromatic-based polymers may be relatively low in value and available for processing. Moreover, in one or more embodiments, such aromatic-based polymers may be dissolved in relatively large quantities in contemplated heavy aromatic materials. The conversion of the heavy aromatics and the aromatic-based polymers may be improved relative to conversion where no aromatic-based polymers are present. For example, in some embodiments, the increase in the formation of BTX may be greater than 20 wt. % when compared to analogous treatment of the one or more aromatic feed chemicals without the addition of the one or more aromatic-based polymers. Accordingly, in one or more embodiments disclosed herein, the relatively good solubility of the aromatic polymers in the heavy aromatic feedstock, coupled with the increased yields of BTX, provide an improvement over past systems for forming BTX.

According to one or more embodiments of the present disclosure, a process for the production of one or more of benzene, toluene, or mixed xylenes may include combining one or more aromatic feed chemicals, one or more aromatic-based polymers, hydrodearylation catalyst, and hydrogen in a hydrodearylation unit to form a chemical product. The one or more aromatic feed chemicals may be chosen from one or more of $C_9+$ alkyl aromatics or alkyl-bridged non-condensed alkyl multi-aromatic compounds. The alkyl-bridged non-condensed alkyl multi-aromatic compounds may include at least two benzene rings connected by an alkyl bridge group having at least two carbons, and the benzene rings may be connected to different carbons of the alkyl bridge group. The process may further include passing the chemical product out of the hydrodearylation unit, wherein the chemical product comprises one or more of benzene, toluene, and mixed xylenes.

According to one or more additional embodiments of the present disclosure a system for the production of one or more of benzene, toluene, or mixed xylenes may include a mixing unit, a hydrodearylation unit comprising a hydrodearylation catalyst and hydrogen, an aromatic feed stream in fluid communication with a mixing unit, an aromatic-based polymer stream in fluid communication with the mixing unit, a mixing unit effluent stream in fluid communication between the mixing unit and the hydrodearylation unit, and a chemical product stream in fluid communication with the hydrodearylation unit, the chemical product stream comprising one or more of benzene, toluene, or mixed xylenes.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

For the purpose of describing the simplified schematic illustrations and descriptions of the relevant figures, the numerous valves, temperature sensors, electronic controllers and the like that may be employed and well known to those of ordinary skill in the art of certain chemical processing operations are not included. Further, accompanying components that are often included in typical chemical processing operations, such as air supplies, catalyst hoppers, and flue gas handling systems, are not depicted. Accompanying components that are in hydroprocessing units, such as bleed streams, spent catalyst discharge subsystems, and catalyst replacement sub-systems are also not shown. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that according to the embodiments presented in the relevant figures, an arrow between two system components may signify that the stream is not processed between the two system components. In other embodiments, the stream signified by the arrow may have substantially the same composition throughout its transport between the two system components. An arrow may indicate that two or more components are in "fluid communication with one another (i.e., operable to pass a fluid between units). Additionally, it should be understood that in one or more embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in some embodiments, less than all of the stream signified by an arrow may be transported between the system components, such as if a slip stream is present.

As used in the present disclosure, an arrow may represent passing a stream or effluent from one unit directly to another unit. For example, an arrow may refer to passing the stream or effluent from the first unit to the second unit without passing the stream or effluent through an intervening reaction system or separation system that substantially changes the composition of the stream or effluent. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent. Combining two streams or effluents together also is not considered to comprise an intervening system that changes the composition of one or both of the streams or effluents being combined. However, arrows, in some embodiments, may not necessarily disclose the direct passing of a stream from one component to another of a given system.

It should be understood that two or more process streams are "mixed" or "combined" when two or more lines intersect in the schematic flow diagrams of the relevant figures. Mixing or combining may also include mixing by directly introducing both streams into a like reactor, separation device, or other system component. For example, it should be understood that when two streams are depicted as being combined directly prior to entering a separation unit or reactor, that in some embodiments the streams could equivalently be introduced into the separation unit or reactor and be mixed in the reactor.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

The present disclosure is directed, according to one or more embodiments described herein, toward systems and methods for the production of benzene, toluene, and/or mixed xylenes (BTX). BTX, as used herein, refers to one or more of benzene, toluene, or mixed xylenes. For example, the production of BTX may refer to the production of any one of benzene, toluene, or mixed xylenes, or any combination of these. As used in this disclosure, the term "mixed xylenes," when used without a designation of the isomer, such as the prefix para, meta, or ortho (or letters p, m, and o, respectively), may refer to one or more of meta-xylene, ortho-xylene, para-xylene, and mixtures of these xylene isomers. Generally, as is described in the embodiments presently disclosed, aromatic feed chemicals may be combined with aromatic-based polymers and hydrodearylated to from BTX.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors such as fixed bed reactors, fluidized bed reactors, ebullated bed reactors, moving bed reactors. An ebullated bed reactor may be a type of fluidized bed reactor with back-mixing of both the reactor liquid composition and catalyst particles throughout the reactor. One or more "reaction zones" may be disposed in a reactor. As used in this disclosure, a "reaction zone" refers to an area where a particular reaction takes place in a reactor. For example, a packed bed reactor with multiple catalyst beds may have multiple reaction zones, where each reaction zone is defined by the area of each catalyst bed.

As used in this disclosure, a "separation unit" refers to any separation device that at least partially separates one or more chemicals that are mixed in a process stream from one another. For example, a separation unit may selectively separate differing chemical species, phases, or sized material from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include, in some embodiments, only partial separation. As used in this disclosure, one or more chemical constituents may be "separated" from a process stream to form a new process stream. Generally, a process stream may enter a separation unit and be divided, or separated, into two or more process streams of desired composition. Further, in some separation processes, a "lesser boiling point fraction" (sometimes referred to as a "light fraction") and a "greater boiling point fraction" (sometimes referred to as a "heavy fraction") may exit the separation unit, where, on average, the contents of the lesser boiling point fraction stream have a lesser boiling point than the greater boiling point fraction stream. Other streams may fall between the lesser boiling point fraction and the greater boiling point fraction, such as a "medium boiling point fraction."

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used in this disclosure, the terms "upstream" and "downstream" may refer to the relative positioning of unit operations with respect to the direction of flow of the process streams. A first unit operation of a system may be considered "upstream" of a second unit operation if process streams flowing through the system encounter the first unit operation before encountering the second unit operation. Likewise, a second unit operation may be considered "downstream" of the first unit operation if the process streams flowing through the system encounter the first unit operation before encountering the second unit operation.

As used in this disclosure, a "catalyst" refers to any substance that increases the rate of a specific chemical reaction. Catalysts described in this disclosure may be utilized to promote various reactions, such as, but not limited to, dearylation. As used in this disclosure, the term "hydrodearylation" refers to a process for the cleaving of the alkyl bridge of alkyl-bridged multi-aromatics or heavy alkyl aromatic compounds to form alkyl mono-aromatics, in the presence a catalyst and hydrogen. A "hydrodearylation catalyst" may refer to a catalyst that promotes dearylation in the presence of hydrogen.

It should further be understood that streams may be named for the components of the stream, and the component for which the stream is named may be the major component of the stream (such as comprising from 50 wt. %, from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "hydrogen stream" passing to a first system component or from a first system component to a second system component should be understood to equivalently disclose "hydrogen" passing to the first system component or passing from a first system component to a second system component.

Figure 1:
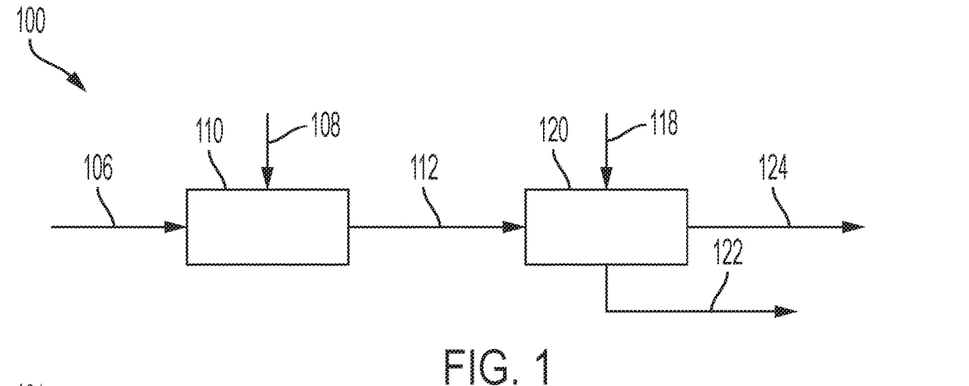
FIG. 1 schematically depicts a system for the production of benzene, toluene, and mixed xylenes, according to one or more embodiments of the present disclosure.

Now referring to FIG. 1, one embodiment of a system 100 for the recovery of benzene, toluene, and/or mixed xylenes is schematically depicted. The system 100 includes a mixing unit 110 operable to mix at least an aromatic feed chemical stream 106 and an aromatic-based polymer stream 108. The system 100 further comprises a hydrodearylation unit 120 downstream of the mixing unit 110. The hydrodearylation unit 120 is operable to dearylate at least a portion of the one or more aromatic feed chemicals and the one or more aromatic-based polymers present in the mixing unit effluent stream 112 to produce a hydrodearylation effluent stream 122.

In one or more embodiments, the aromatic feed chemical stream 106 comprises one or more aromatic feed chemicals. For example, the aromatic feed chemical stream 106 may comprise at least 50 wt. %, at least 75 wt. %, at least 90 wt. %, at least 95 wt. %, at least 99 wt. %, or may consist or consist essentially of one or more aromatic feed chemicals. The one or more aromatic feed chemicals may be chosen from one or more of $C_9+$ alkyl aromatics or alkyl-bridged non-condensed alkyl multi-aromatic compounds. The aromatic feed chemical stream 106 may be a product stream from an aromatic complex, as is described herein.

In one or more embodiments, the aromatic feed chemical stream 106 may comprise one or more of $C_9+$ alkyl aromatics. As described herein, alkyl aromatics refer to compounds that consist of an aromatic moiety and one or more alkyl moieties. The alkyl moieties may be straight-chained or branched. As described herein, $C_9+$ compounds include at least 9 carbon atoms. In general, and as used herein, $C_x$ refers to hydrocarbons having x carbon atoms, and $C_x+$ refers to hydrocarbons having at least x carbon atoms. Examples of $C_9+$ compounds include, without limitation, trimethylbenezes (e.g., 1,3,5-trimethylbenzene), methylethylbenzenes/ethyltoluene (e.g., 1-methyl-2-ethylbenzene), condensed di-aromatics (e.g., alkylated naphthalene), non-condensed di-aromatics (e.g., alkylated biphenyls), or $C_{16}+$ non-condensed alkylated di-aromatics.

The alkyl-bridged non-condensed alkyl multi-aromatic compounds may include at least two benzene rings connected by an alkyl bridge group having at least two carbons, wherein the benzene rings are connected to different carbons of the alkyl bridge group. The one or more aromatic feed chemicals may be from one or more hydrocarbon treatments in a petroleum refinery. In one or more embodiments, the one or more aromatic feed chemicals may comprise a heavy aromatics stream from a unit operation of a petroleum refinery.

By way of example and not limitation, the alkyl-bridged non-condensed multi-aromatic compounds may include a mixture of chemical compounds illustrated by Formula I, Formula II, and Formula III, and various combinations of these compounds.

[Formula I]

[Formula II]

[Formula III]

In Formulas I, II, and III, $R_2$, $R_4$, and $R_6$ are alkyl bridge groups independently having from two to six carbon atoms. $R_1$, $R_3$, $R_5$, and $R_7$ are independently selected from the group consisting of hydrogen and an alkyl group having from one to eight carbon atoms so long as Formulas I, II, and II have at least sixteen carbon atoms. In addition to the groups $R_1$, $R_3$, $R_5$, and $R_7$, the benzene groups of Formulas I, II, and III may further include additional alkyl groups connected to the benzene groups, respectively. In addition to the four benzene groups of Formula III, the various alkyl aromatic compounds may include five or more benzene groups connected by alkyl bridges, where the additional benzene groups further may include alkyl groups connected to the additional benzene groups.

In one or more embodiments, the one or more aromatic feed chemicals may be a heavy aromatic, such as $C_9+$ or $C_{10}+$ hydrocarbons from a xylene rerun column or a heavy aromatic column bottoms from a para-xylene aromatic complex. The one or more aromatic feed chemicals may include $C_9$ to $C_{16}+$, and the one or more aromatic feed chemicals may be predominantly mono-aromatics, di-aromatics, and poly-aromatics.

In one or more embodiments, the aromatic-based polymer stream 108 may include one or more aromatic-based polymers. As used in this disclosure, the term "aromatic-based polymers" refers to a polymer where at least 50% of the units (such as monomeric units) comprise an aromatic moiety. In some embodiments, aromatic-based polymers may comprise, but are not limited to, polystyrene, polyphenylene, poly(p-xylene), poly(phenylenevinylene), polybenzyl, or combinations thereof.

In one or more embodiments, the aromatic-based polymer may be a solid and the aromatic feed chemicals may be liquid. The aromatic-based polymer stream 108 may be combined with the aromatic feed chemical stream 106 at or near the saturation point of the aromatic-based polymers in the aromatic feed chemical stream 106. Adding the one or more aromatic-based polymers of the aromatic-based polymer stream 108 to the one or more aromatic feed chemicals of the aromatic feed chemical stream 106 at or near its saturation point may allow the highest amount of the one or more aromatic-based polymers to be dissolved in the one or more aromatic feed chemicals. In some embodiments, the weight ratio of the one or more aromatic-based polymers to the one or more aromatic feed chemicals may be greater than 1:1000, such as between 1:1000 to 1:1. In some embodiments, the percentage mass of the one or more aromatic-based polymers to the one or more aromatic feed chemicals may range 0.1 wt. % to 50 wt. %. In some embodiments, the weight ratio of the one or more aromatic-based polymers to the one or more aromatic feed chemicals may be about 1:20.

In some embodiments, the amount of aromatic-based polymer mixed with the aromatic feed chemicals is at least 90%, at least 95%, or even at least 99% of the amount of aromatic-based polymer needed to achieve maximum saturation (i.e., the point where no more solid polymer may be dissolved as the solution is saturated). The maximum saturation may depend upon the temperature, pressure, or other conditions in the mixing vessel. The aromatic feed chemical stream 106 and the aromatic-based polymer stream 108 may be passed to the mixing unit 110, where the aromatic feed chemical stream 106 and the aromatic-based polymer stream 108 are combined. The mixing unit 110 may be any vessel or other like apparatus suitable for mixing two or more chemical streams. The mixing unit 110 may include a mixer, such as an agitator. The first mixing unit effluent stream 112 may include the mixed components of aromatic feed chemical stream 106 and aromatic-based polymer stream 108, and may be passed from the mixing unit 110 to the hydrodearylation unit 120. In one or more embodiments, the mixing unit may operate at a temperature of less than or equal to 300° C. For example, the mixing unit may operate at a temperature of less than or equal to 200° C., or even less than or equal to 100° C. The mixing unit may operate at room temperature or greater (~25° C. or greater), or greater than or equal to 50° C. In one or more embodiments, the mixing unit may operate at a pressure of from 1 bar to 200 bars. For example, the mixing unit may operate at a pressure of from 1 bar to 150 bars, from 1 bar to 100 bars, from 1 bar to 80 bars, from 1 bar to 50 bars, from 1 bar to 20 bars, from 1 bar to 10 bars, or at a pressure of from 1 bar to 3 bars.

In some embodiments, such as shown in FIG. 1, stream 118 may comprise hydrogen and may be passed to the hydrodearylation unit 120. In alternative embodiments, the hydrogen of stream 118 may be combined with the aromatic feed chemical stream 106, the aromatic-based polymer stream 108, or the first mixing unit effluent stream 112 anywhere upstream of the hydrodearylation unit 120. The hydrogen of stream 118 may be combined at a rate of 100 to 2500 standard liters per liter of the one or more aromatic feed chemicals of the aromatic feed chemical stream 106.

In one or more embodiments, the hydrogen of stream 118 may include recycled hydrogen and/or makeup hydrogen. In one or more embodiments, the recycled hydrogen may be a stream from the processing of a product stream from the hydrodearylation unit 120. In one or more embodiments, the hydrogen of stream 118 may comprise at least 70 mole percent hydrogen, at least 90 mole percent hydrogen, at least 95 mole percent hydrogen, or even at least 99 mole percent hydrogen. In other embodiments, the hydrogen of stream 118 may comprise any percentage meeting the hydrogen partial pressure requirement of the hydrodearylation unit 120.

The hydrodearylation unit 120 may be a reactor operable to dearylate the one or more of the components of first mixing unit effluent stream 112 in the presence of hydrogen. A hydrodearylation catalyst may be combined with the contents of the aromatic feed chemical stream 106, the aromatic-based polymer stream 108, and the hydrogen of stream 118, or the first mixing unit effluent stream 112 in the hydrodearylation unit 120. They hydrodearylation catalyst may be operable to promote a dearylation reaction in the hydrodearylation unit 120.

In one or more embodiments, the hydrodearylation catalyst may be positioned in the hydrodearylation unit 120, such in a fixed bed arrangement, an ebullated bed arrangement, or a moving bed arrangement. The hydrodearylation unit 120 may comprise a single catalyst bed or multiple catalyst beds and may receive quench hydrogen in between the beds of a multi-bed arrangement. Although not shown, the quench hydrogen may be a portion of the hydrogen of stream 118 piped to the various locations of the catalyst beds in the hydrodearylation unit 120.

In one or more embodiments, the hydrodearylation unit 120 may include two or more reactors in series or in parallel and may be used with an in-situ regeneration loop. As a fixed bed catalyst system is susceptible to coking when processing heavy aromatic chemicals, one reactor may be operating while the other reactor is in a regeneration mode for various embodiments.

In one or more embodiments, the degree of conversion in the hydrodearylation unit 120 may be kept below a threshold to limit the amount of catalyst required and the amount of coking on the catalyst. By way of example and not limitation, a threshold limit may be 70% of a maximum potential conversion in the hydrodearylation unit 120. In one or more embodiments, operating conditions for the hydrodearylation unit 120 may include a reaction temperature in the range of from 200° C. to 450° C., and a hydrogen partial pressure in the range of from 1 bar gauge to 80 bar gauge.

The hydrodearylation catalyst may comprise a support comprising one or more of silica, alumina, titania and combinations thereof. The hydrodearylation catalyst may further comprise an acidic component comprised of one or more of amorphous silica-alumina, zeolite, and combinations thereof. In one or more embodiments, the hydrodearylation catalyst may further include at least one IUPAC Group 8-10 metal, and at least one IUPAC Group 6 metal. The IUPAC Group 8-10 metal may be selected from the group consisting of iron, cobalt, and nickel, and combinations thereof. The IUPAC Group 6 metal may be selected from a group consisting of molybdenum and tungsten, and combinations thereof. The IUPAC Group 8-10 metal may be present in an amount of approximately 2-20% by weight, and the IUPAC Group 6 metal may be present in an amount of approximately 1-25% by weight. In one or more embodiments, the IUPAC Group 8-10 and IUPAC Group 6 metals may be on a support material. In one or more embodiments, a support material of the hydrodearylation catalyst may be silica or alumina or titania, and may further include an acidic component selected from the group consisting of an amorphous silica alumina, a zeolite or a combination of the two. In one or more embodiments, the hydrodearylation unit 120 may contain a catalyst having any noble IUPAC Group 8-10 metal on a silica-alumina or alumina support having an acid cracking component of an amorphous silica-alumina or a zeolite, or a combination of the two. In certain embodiments, the hydrodearylation unit 120 may contain a catalyst selected from the group consisting of platinum, palladium, and combinations thereof, on a silica-alumina or alumina support having an acid cracking component of an amorphous silica-alumina or a zeolite, or a combination of the two.

Upon combining one or more aromatic feed chemicals of the aromatic feed chemical stream 106, one or more aromatic-based polymers of the aromatic-based polymer stream 108, hydrodearylation catalyst, and hydrogen of stream 118 to the hydrodearylation unit 120, a hydrodearylation reaction may occur under suitable reaction conditions. In such a reaction, the alkyl bridges of the one or more aromatic feed chemicals may be cleaved to produce benzene, toluene, and mixed xylenes. In one or more embodiments, non-bridging alkyl groups connected to the benzene rings of the one or more aromatic feed chemicals may remain connected to the benzene rings of the one or more aromatic feed chemicals in the chemical product. By way of example and not limitation, the chemical product may include a mixture of chemical compounds illustrated by Formula IV.

[Formula IV]

For the various chemical products, in Formula IV, $R_1$ and $R_2$ are independently selected from the group consisting of hydrogen and an alkyl group having from one to eight carbon atoms.

The hydrodearylation unit 120 may be a single reactor, or may be a plurality of reactors, either in series or in parallel. The process may comprise operating the hydrodearylation unit 120 at a temperature of from 200 to 450° C., or, in some embodiments, about 350° C. The process may comprise supplying hydrogen to the hydrodearylation unit 120 at a partial pressure in the range of 1 to 100 bar, or in the range of 10 to 80 bar. In one or more embodiments, a liquid hourly space velocity of the hydrodearylation unit 120 may be 0.5 to 10 per hour.

The systems and processes of the present disclosure may enable increased benzene, toluene, and mixed xylenes production through the addition of one or more aromatic-based polymers to the one or more aromatic feed chemicals during dearylation. In one or more embodiments, when compared to analogous treatment of the one or more aromatic feed chemicals without the addition of the one or more aromatic-based polymers, the addition of the one or more aromatic-based polymers to the one or more aromatic feed chemicals results in an increase in the formation of benzene, toluene, and mixed xylenes.

In embodiments, a chemical product may be passed out of the hydrodearylation unit 120 in the chemical product stream 122 (sometimes referred to herein as a "dearylation effluent"). In one or more embodiments, the chemical product stream 122 may comprise one or more of benzene, toluene, and/or mixed xylenes. Generally, the amount of benzene, toluene, and/or mixed xylenes is greater in the chemical product stream 122 than in the aromatic feed chemical stream 106, the aromatic-based polymer stream 108, and the mixing unit effluent stream 112. For example, the aromatic feed chemical stream 106 or the first mixing unit effluent stream 112 may include less than 1 wt. % BTX. The chemical product stream 122 may include at least 15 wt. %, at least 20 wt. %, or even at least 25 wt. % BTX.

In one or more embodiments, gas may be passed out of the hydrodearylation unit 120 via stream 124. The gas effluent of stream 124 may include hydrogen (which may be recycled) or other hydrocarbon gasses.

In some embodiments, the processes may further comprise combining recycled aromatic chemicals in the hydrodearylation unit 120. In other embodiments, the recycled aromatic chemicals may be separated from the chemical product stream 122. The recycled aromatic chemicals may be combined with the one or more aromatic feed chemicals upstream of the hydrodearylation unit 120 to form a combined aromatic chemical feed that is fed to the reactor.

Figure 2:
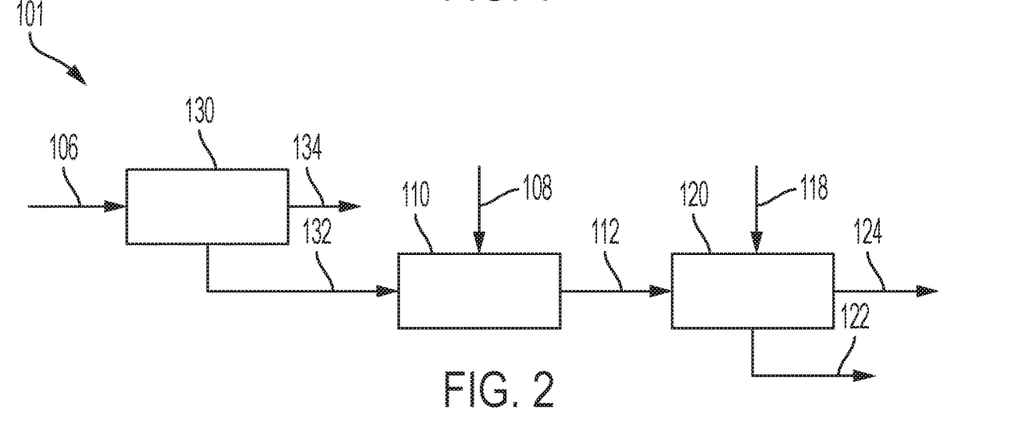
FIG. 2 schematically depicts another system for the production of benzene, toluene, and mixed xylenes, according to one or more embodiments of the present disclosure.

Referring now to FIG. 2, system 101 is depicted. System 101 is similar in many respects to system 100 of FIG. 1. However, notably, system 101 further includes a separation unit 130. In one or more embodiments, the separation unit 130 may be an atmospheric distillation unit, such as a flash drum operating at or near atmospheric pressure. The separation unit 130 may separate the aromatic feed chemical stream 106 into a light aromatic chemical stream 134 and a heavy aromatic chemical stream 132. The cut point (at atmospheric conditions) of streams heavy aromatic chemical stream 132 and light aromatic chemical stream 134 may be in a range of from 160° C. to 200° C., such as from 170° C. to 190° C., from 175° C. to 185° C., or about 180° C. In some embodiments, the light aromatic chemical stream 134 may have a final boiling point equal to the cut point (or cut point range) of the separation unit 130. The heavy aromatic chemical stream 132 may have an initial boiling point equal to the cut point of the separation unit 130. The light aromatic chemical stream 134 may include $C_{10-}$ hydrocarbons such as gasoline. The heavy aromatic chemical stream 132 may include $C_{11}+$ hydrocarbons. In such embodiments, system 101 essentially functions like system 100 but utilizes an aromatic feed that is relatively heavy (e.g., including only $C_{11}+$ compounds). It should be understood that in embodiments such as those of FIG. 2, the heavy aromatic chemical feed stream 132 may be referred to as an aromatic feed chemical.

The heavy aromatic chemical stream 132 may be passed to the mixing unit 110, while the light aromatic chemical stream 134 may be passed to another downstream process. The heavy aromatic chemical stream 132 may be combined in the mixing unit 110 with the aromatic-based polymer stream 108. The first mixing unit effluent stream 112 may be combined in the hydrodearylation unit 120 with the hydrogen of stream 118 and hydrodearylation catalyst to produce a chemical product stream 122 and a gas effluent 124, similar to the process of system 100.

Figure 3:
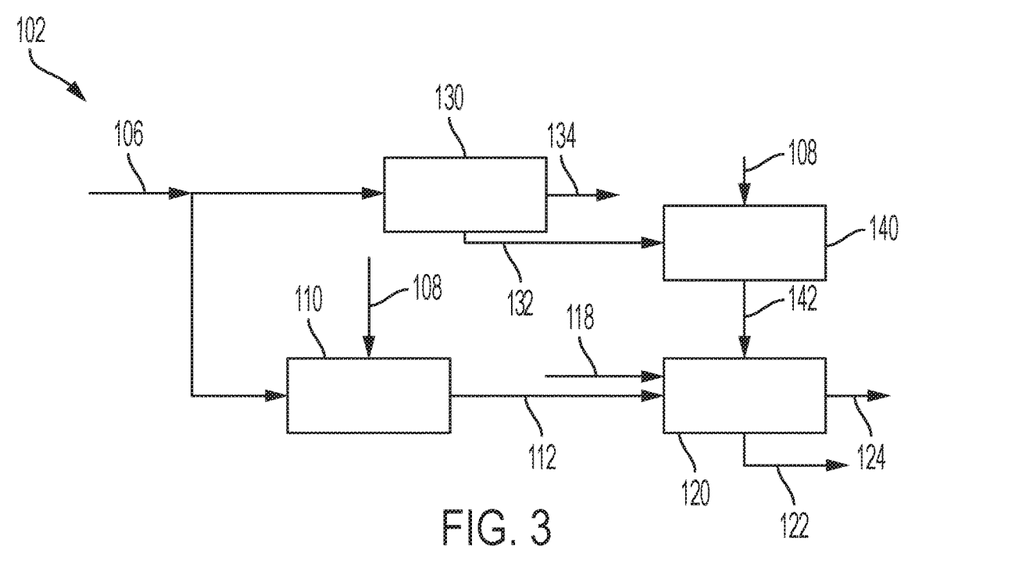
FIG. 3 schematically depicts another system for the production of benzene, toluene, and mixed xylenes, according to one or more embodiments of the present disclosure.

Referring now to FIG. 3, system 102 is depicted, which is similar in many respects to systems 100 and 101 of FIGS. 1 and 2, respectively, but divides the aromatic feed chemical stream 106 into two portions, where one portion is passed to the mixing unit 110 (similar to system 100) and the other portion is passed to the separation unit 130 (similar to system 101). Such a system may include two mixing units, the mixing unit 110 and a second mixing unit 140. A portion of the aromatic feed chemical stream 106 may be fed directly to a mixing unit 110, while the heavy aromatic chemical stream 132 from the separation unit 130 may be fed to the second mixing unit 140. The heavy aromatic chemical stream 132 from the separation unit 130 may be mixed with the aromatic-based polymer stream 108 in the second mixing unit 140. A first mixing unit effluent stream 112 and a second mixing unit effluent 142 may be combined in the hydrodearylation unit 120 with the hydrogen of stream 118 and hydrodearylation catalyst to produce the chemical product stream 122 and the gas effluent 124.

Figure 4:
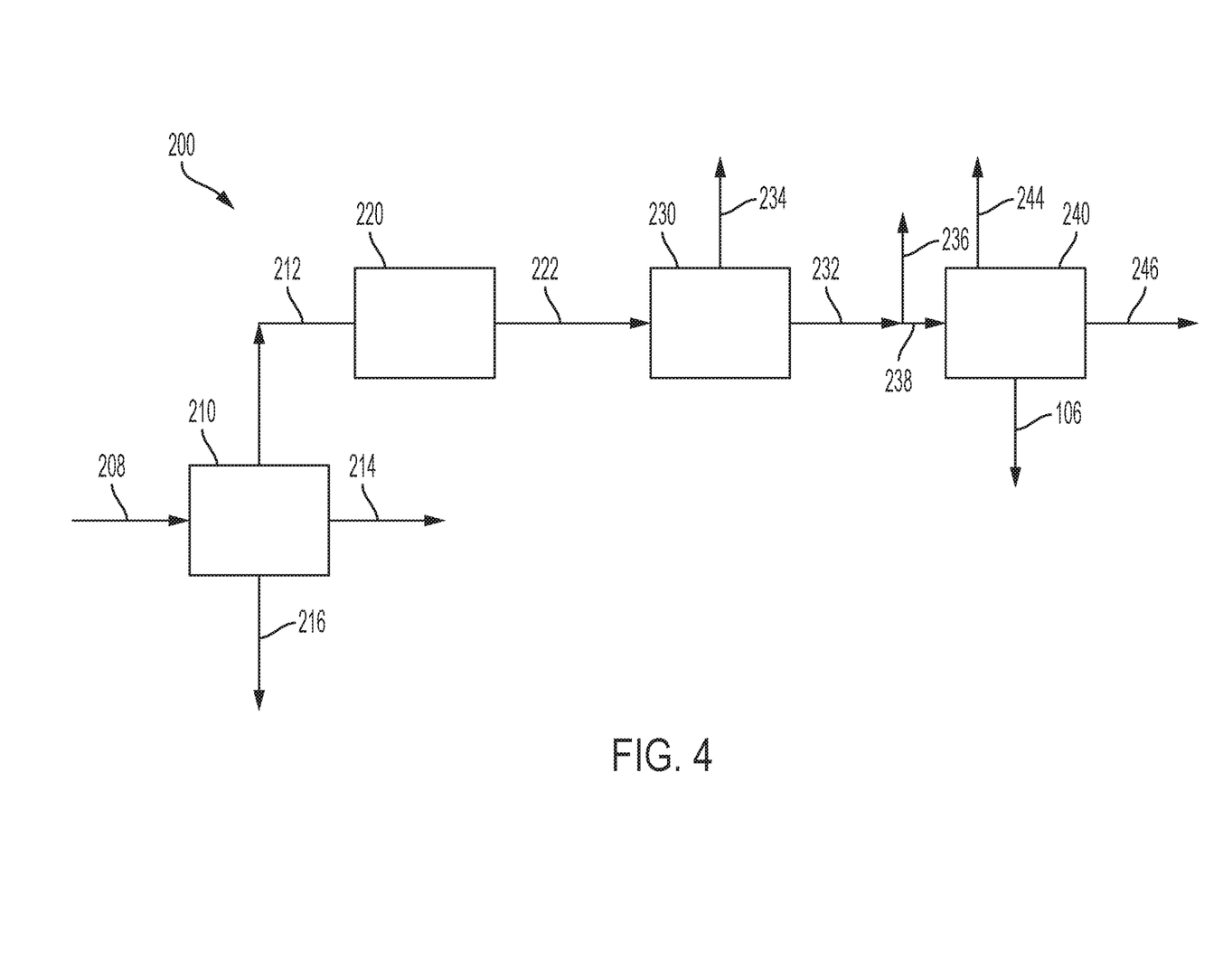
FIG. 4 schematically depicts an upstream processing system, according to one or more embodiments of the present disclosure.

Referring now to FIG. 4, in some embodiments, the aromatic feed chemical stream 106 may be from an upstream process 200 of a refinery. The upstream process 200 may comprise an atmospheric distillation unit 210, a naphtha hydrotreating unit 220, a naphtha reforming unit 230, and an aromatic complex 240. The atmospheric distillation unit 210 may be upstream of the naphtha hydrotreating unit 220. The naphtha hydrotreating unit 220 may be downstream of the atmospheric distillation unit 210 and upstream of the naphtha reforming unit 230. The naphtha reforming unit 230 may be downstream of the naphtha hydrotreating unit 220 and upstream of the aromatic complex 240. The aromatic complex 240 may be downstream of the naphtha reforming unit 230.

In the upstream process 200, crude oil 208 may be fed to the atmospheric distillation unit 210. The atmospheric distillation unit may be operable to produce naphtha 212, diesel 214, and atmospheric residue 216. The naphtha 212 may be fed to the naphtha hydrotreating unit 220, which may be operable to produce hydrotreated naphtha 222. The hydrotreated naphtha 222 may be fed to the naphtha reforming unit 230. Optionally, light naphtha ($C_5$-$C_6$) may be separated from the hydrotreated naphtha 222 and the resulting heavy naphtha ($C_7+$) is sent to the naphtha reforming unit 230. The naphtha reforming unit 230 may be operable to produce a reformate 232 and a hydrogen effluent 234. A portion 236 of the reformate 232 may be separated from the reformate 232 produced by the naphtha reforming unit 230 for further processing. The remaining portion 238 of the reformate 232 may be fed to an aromatic complex 240. The aromatic complex 240 may be operable to produce one or more aromatic feed chemicals, a gasoline pool 244, $C_{9-}$ aromatics 246, and the aromatic feed chemical stream 106. The one or more aromatic feed chemicals produced from the aromatic complex 240 may then be fed to systems 100, 101, or 102 of FIG. 1-3.

Figure 5:
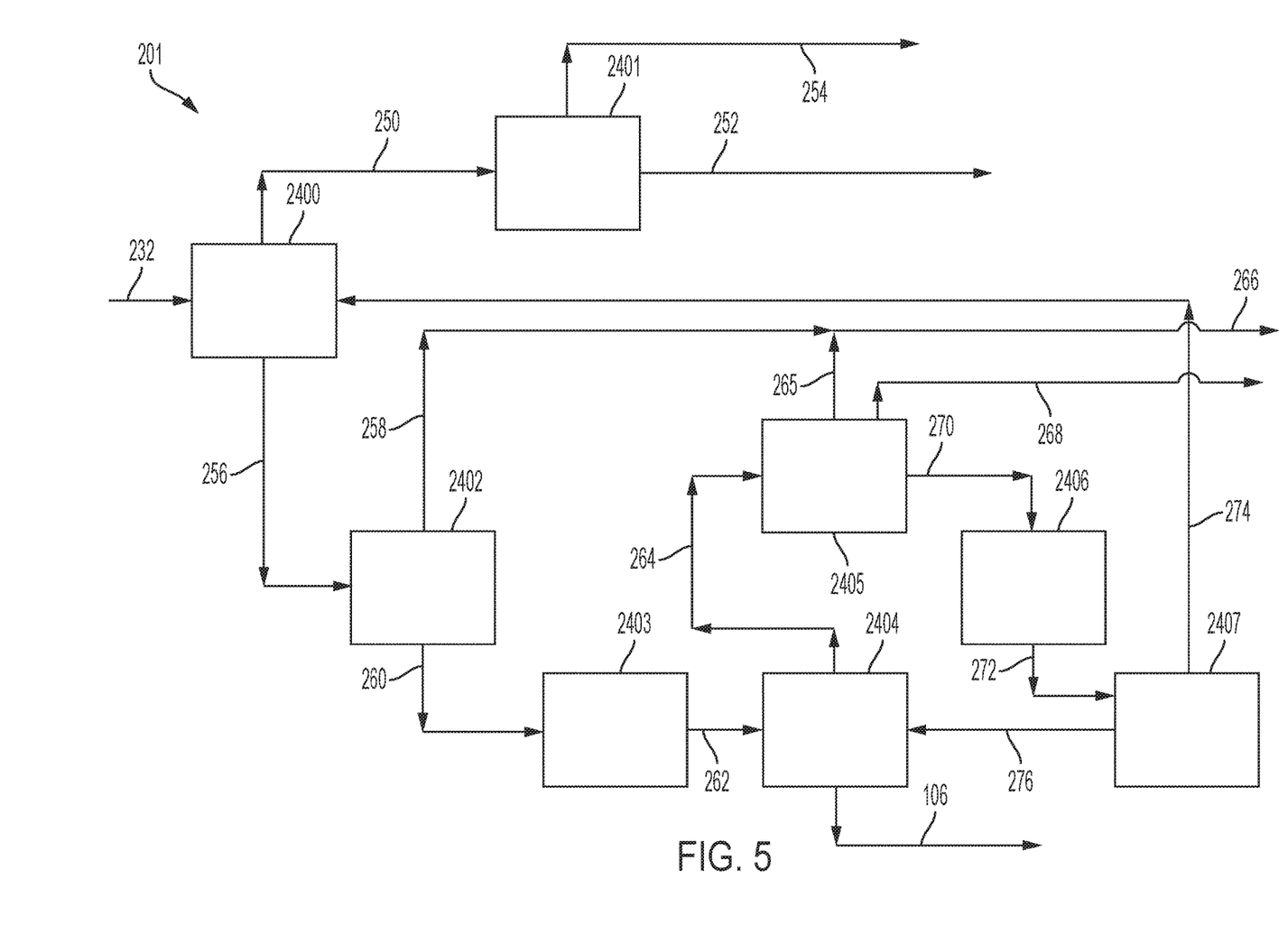
FIG. 5 schematically depicts an aromatics complex, according to one or more embodiments of the present disclosure.

Referring to FIG. 4-5, in some embodiments, the reformate 232 from the naphtha reforming unit 230 may be processed in an aromatic complex system 201. Referring to FIG. 5, the reformate 232 may be fed to a reformate splitter 2400, where the reformate 232 may be split into two fractions, a light reformate fraction 250 comprising $C_5$-$C_6$ hydrocarbons and a heavy reformate fraction 256 comprising $C_{7+}$ hydrocarbons. The light reformate fraction 250 may be fed to benzene extraction unit 2401. The benzene extraction unit 2401 may process the light reformate fraction 250 to produce benzene 252 and benzene-free gasoline in raffinate motor gasoline (mogas) 254. The heavy reformate fraction 256 may be fed to a first splitter 2402. The first splitter 2402 may process the heavy reformate fraction 256 to produce a first $C_7$ mogas fraction 258 and a $C_{8+}$ hydrocarbon fraction 260.

The $C_{8+}$ hydrocarbon fraction 260 may be fed to a clay treater 2403. The clay treater 2403 may process the $C_{8+}$ hydrocarbon fraction 260 to produce a clay treated $C_{8+}$ hydrocarbon fraction 262. The clay treated $C_{8+}$ hydrocarbon fraction 262 may be fed to a xylene rerun unit 2404. The xylene rerun unit 2404 may process the clay treated $C_{8+}$ hydrocarbon fraction 262 to produce a $C_{9+}$ hydrocarbon fraction, which is the aromatic feed chemical stream 106 of FIG. 1-4, and a $C_8$ hydrocarbon fraction 264. The $C_8$ hydrocarbon fraction 264 may be fed to a p-xylene extraction unit 2405. The p-xylene extraction unit 2405 may process the $C_8$ hydrocarbon fraction 264 to produce a second $C_7$ mogas fraction 265, a first p-xylene fraction 268, and an isomerized xylene fraction 270. The first $C_7$ mogas fraction 258 and second $C_7$ mogas fraction 265 may be combined to form a $C_7$ mogas product 266.

The isomerized xylene fraction 270 may be fed to xylene isomerization unit 2406. The xylene isomerization unit 2406 may process the isomerized xylene fraction 270 to produce a second p-xylene fraction 272. The second p-xylene fraction 272 may be fed to a second splitter 2407. The second splitter 2407 may process the second p-xylene fraction 272 to produce an unconverted p-xylene fraction 274 and a converted p-xylene fraction 276. The unconverted p-xylene fraction 274 may be recycled back to the reformate splitter 2400. The converted p-xylene fraction 276 may be fed to the xylene rerun unit 2404. The xylene rerun unit 2404 may combine the clay treated $C_{8+}$ hydrocarbon fraction 262 and converted p-xylene fraction 276 to produce a $C_{9+}$ hydrocarbon fraction which is the one or more aromatic feed chemicals.

Figure 6:
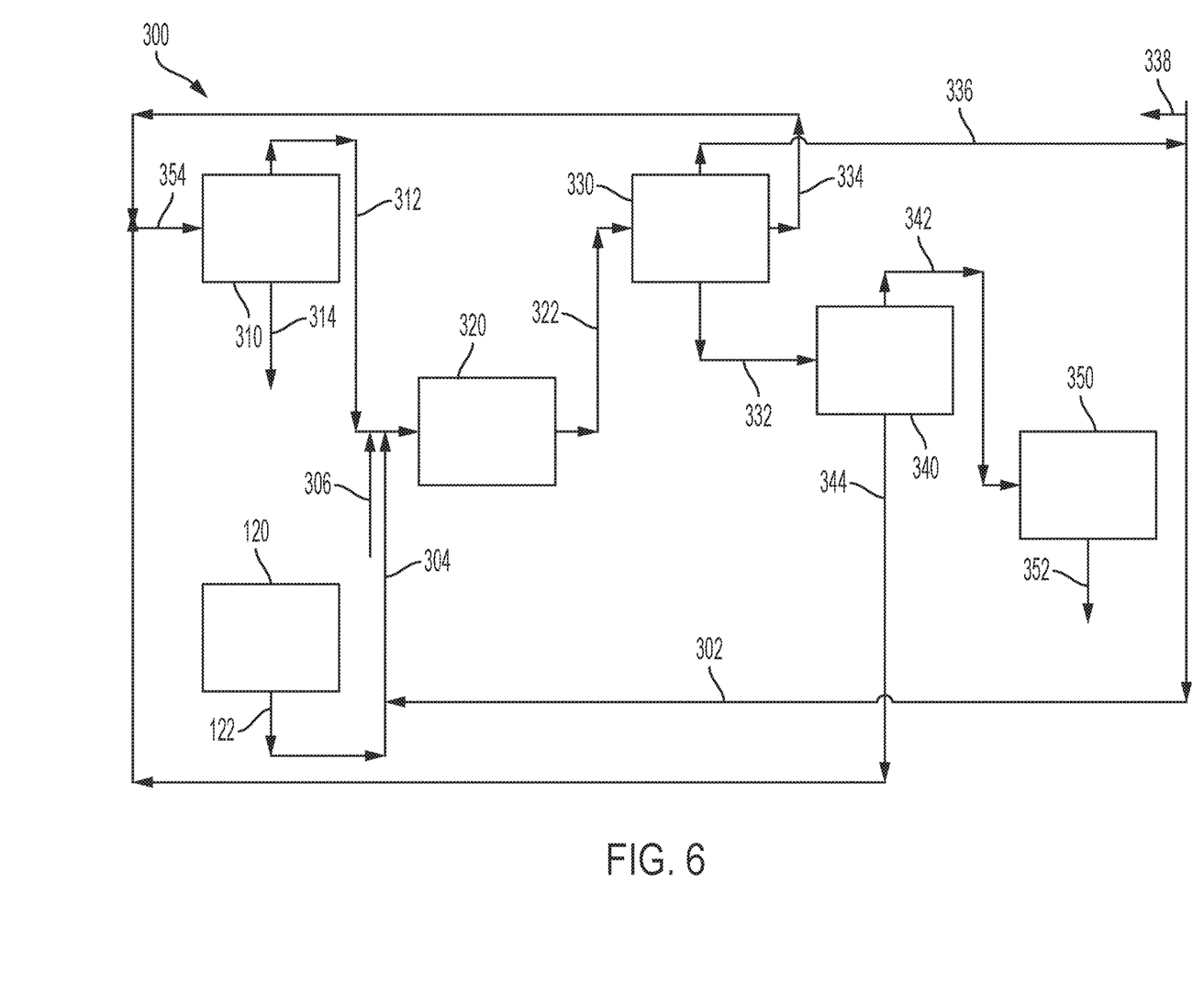
FIG. 6 schematically depicts a downstream processing system, according to one or more embodiments of the present disclosure.

In one or more embodiments, the hydrodearylation effluent 122 may be further processed in a downstream system, such as that depicted in FIG. 6. The hydrodearylation effluent 122 of systems 101, 102, 103 of FIGS. 1-3 may be passed to downstream system 300, which may be a para-xylene recovery unit. Referring to FIG. 6, in some embodiments, the hydrodearylation effluent 122 may be recovered from the hydrodearylation unit 120 and processed in a downstream system 300. In some embodiments, the downstream system may be a para-xylene recovery system such as shown in FIG. 6. The hydrodearylation effluent 122, exiting from the hydrodearylation unit 120, may also contain benzene, toluene and $C_8$ compounds, along with $C_{9+}$ alkyl aromatics. The hydrodearylation effluent 122 may be mixed with benzene 302 to form a feed 304. The feed 304 may be supplied to a transalkylation reactor 320 either with or without additional hydrogen 306. The feed 304 in the presence of a catalyst may be converted to a first product 322 comprising benzene, $C_{8+}$ aromatics including ethylbenzene and xylenes, and toluene. The first product 322 from the transalkylation reactor may be directed to a first separation column 330. The first product 322 may be separated into three fractions: a first overhead fraction 336 comprising benzene, a first bottoms fraction 332 comprising $C_{8+}$ aromatics including ethylbenzene and xylenes, and a side-cut fraction 334 containing toluene. The first overhead fraction 336 may be recycled via stream 302 to the first transalkylation unit 320 after benzene may be removed via a purge 338. The first bottoms fraction 332 comprising $C_{8+}$ aromatics, including ethylbenzene and xylenes, from the first separation column 330 may be directed to a second separation column 340. Two fractions are recovered from this second separation column 340: a second overhead fraction 342 comprising ethylbenzene and xylenes, which may be directed to a para-xylene unit 350 to produce a para-xylene-rich fraction 352, and a second bottoms fraction 344 comprising $C_{9+}$ alkyl aromatics. The side-cut fraction 334 from the first separation column 330 may be supplied as part of a combined feed 354 to a third separation column 310 after additional toluene may be added or removed (not shown in FIG. 6). Toluene may be normally recycled to extinction by reacting with $C_9$ and $C_{10}$ to produce benzene and $C_8$. If there may be a decrease or lack of toluene in the system, make-up toluene may be required. If there may be a decrease or lack of $C_9/C_{10}$, the amount of toluene can be proportionately reduced to correct the stoichiometry. Certain market conditions may influence the removal of toluene from the system. The side-cut fraction 334 may be mixed with the second bottoms fraction 344 comprising $C_{9+}$ alkyl aromatics to form a combined feed 354 that may be supplied to the third separation column 310. Two streams are recovered from this third separation column 310: a third bottoms fraction 314 of $C_{11+}$ alkyl aromatics and an overhead fraction 312 of $C_9$ and $C_{10}$ alkyl aromatics and lighter compounds (including $C_7$ alkyl aromatics) directed to the transalkylation unit 320. In certain embodiments, the unconverted products can be recycled to the hydrodearylation unit 120 (not shown in FIG. 5).

EXAMPLES

The various embodiments of methods and systems for the processing of aromatic feeds will be further clarified by the following examples. The examples are illustrative in nature, and should not be understood to limit the subject matter of the present disclosure.

Background on Determination of Solubility

Solubility is a chemical property referring to the ability for a given substance, the solute, to dissolve in a solvent. It is measured in terms of the maximum amount of solute dissolved in a solvent at equilibrium. The resulting solution is called a saturated solution. The solubility of a substance fundamentally depends on the physical and chemical properties of the solute and solvent as well as on temperature, pressure and presence of other chemicals (including changes to the pH or acidity) of the solution. The extent of the solubility of a substance in a specific solvent is measured as the saturation concentration, where adding more solute does not increase the concentration of the solution and begins to precipitate the excess amount of solute.

The Hildebrand solubility parameter (HSP), δ, provides a numerical estimate of the degree of interaction between materials and can be a good indication of solubility, particularly for nonpolar materials such as many polymers. Materials with similar values of δ are likely to be miscible.

The aromatic bottoms stream from the aromatic recovery complex possess a high solubility factor compared with other straight run petroleum fractions. The Hildebrand solubility scale (Joel H. Hildebrand, Journal of Paint Technology, Vol. 39, No. 505, February 1967) is one of the oldest and widely accepted scales used in the industry to scale the solvents. The Hildebrand solubility parameter is derived from the cohesive energy density of the solvent, which in turn is derived from the heat of vaporization. At a fundamental level, the Hildebrand solubility parameter explains that as a liquid is heated to its boiling point, energy is added to the liquid, resulting in an increase in the temperature of the liquid. However, once the liquid reaches its boiling point, the further addition of heat does not cause any additional increase in temperature. This energy that is subsequently added separates the molecules of the liquid, which may boil them away as gas. If the amount of energy (in calories) added from the onset of boiling to the point when all the liquid has boiled away is totaled, it will have a direct indication of the amount of energy required to separate the liquid into a gas, and thus the amount of van der Waals forces that holding the molecules of the liquid together. The energy required to vaporize the liquid is called the heat of vaporization. From the heat of vaporization, in calories per cubic centimeter of liquid, the cohesive energy density can be derived by the following expression:

$$c = \frac{\Delta H - R * T}{Vm}$$

Where:

c=Cohesive Energy Density

ΔH=Heat of Vaporization

R=Gas Constant

T=Temperature $V_m$=Molar Volume

The Hildebrand solubility parameter, δ, is equivalent to the square root of the cohesive energy density as a numerical value indicating the solvency behavior of a specific solvent. However, since solubility parameters are not readily available, the solubility parameters for the aromatic bottoms streams were calculated as shown in Table 1. The typical HSPs for the individual solvents are also shown in Table 1. Also shown in Table 1, are the HSPs of the aromatic bottoms from an aromatic complex, which may be used as the feed in the presently disclosed embodiments.

TABLE 1

| Solvent | $\delta = MPa^{1/2}$ |
|---|---|
| Heptane | 15.3 |
| n-Dodecane | 16.0 |
| Benzene | 18.7 |
| Kerosene | 16.3 |
| Light Gas Oil | 15.7 |
| Aromatic Bottoms (Full Range) | 20.7 |
| Aromatic Bottoms 180° C.+ | 21.2 |

As seen, heptane, a paraffinic solvent with a carbon number of seven has a HSB of 15.3 and n-dodecane, a paraffinic solvent with carbon number of twelve has a HSB value of 16. Benzene, a mono-aromatic solvent with a carbon number of six has a HSB value of 18.7. Kerosene's HSB is 16.3 showing that it is composed of paraffinic and aromatic components. Light gas oil seems to be more paraffinic in nature based on the HSB compared with the kerosene fraction. The aromatics bottoms stream, whether its full range stream as-received from an aromatic recovery complex, or the fraction boiling above 180° C., exhibit high HSB values in the range 20.7-21.7. Based on the HSB values, it is observed that the one or more aromatic feed chemicals obtained from an aromatic complex is a powerful solvent and has good blending properties.

Example 1: Mixing an Aromatic Polymer with an Aromatic Chemical

In Example 1, an aromatic base polymer, polystyrene (commercially available as Styrofoam from Dow), was dissolved in an aromatic chemical. The polystyrene features an estimated Mw of 233,600 g/mol (measured by gel permeation chromatography). The properties of the aromatic chemical, both with and without the addition of polystyrene, is shown in Table 2.

TABLE 2

| Property | Aromatic Chemical (without Aromatic Polymer) | Aromatic Chemical (with Aromatic Polymer) |
|---|---|---|
| Density (g/mL) | 0.9819 | 0.9786 |
| Initial Boiling Point (IBP) (° C.) | 198 | 131 |
| 10 wt. % Boiling Point (BP) (° C.) | 211 | 196 |
| 30 wt. % BP (° C.) | 236 | 223 |
| 50 wt. % BP (° C.) | 274 | 263 |
| 70 wt. % BP (° C.) | 302 | 291 |
| 90 wt. % BP (° C.) | 329 | 317 |
| Final Boiling Point (FBP) | 400 | 391 |
| Paraffins (wt. %) | 0.1 | 0.1 |
| Mono-Naphthenes (wt. %) | 0.1 | 0.1 |
| Di-Naphthenes (wt. %) | 0.1 | 0.1 |
| Mono Aromatics (wt. %) | 10.75 | 10.2 |
| Naphtheno Mono Aromatics (wt. %) | 12.1 | 11.5 |
| Diaromatics (wt. %) | 65.8 | 62.5 |
| Naphtheno Di Aromatics (wt. %) | 6.9 | 6.6 |
| Tri/Tetra Aromatics (wt. %) | 4.3 | 4.1 |
| Benzene, Toluene, Xylene (wt. %) | 0.1 | 0.1 |
| Non-GC Compatible Material (wt. %) | N/A | 4.8 |

After dissolving the polystyrene in the aromatic chemical, thermogravimetric analysis of the polystyrene under air resulted in the following heat loss profile: at 230° C., 99.7% of the mass of the polystyrene was retained; at 344° C., the polystyrene exhibits its on-set temperature; at 393° C., the polystyrene exhibited its maximum decomposition temperature; at 600° C., the polystyrene had lost 95.6% of its mass; and at 900° C., the polystyrene had lost 96.0% of its mass. In the aromatic chemical with the aromatic polymer, the 4.8 wt. % non-gas chromatography compatible material may refer to the aromatic polymer.

Further, Table 2 shows that the amount of benzene, toluene, and xylene in the aromatic chemicals, with and without the addition of the aromatic polymer, is just 0.1 wt. %. In Table 2, the non-GC compatible material corresponds to material that may be too large to be detected by gas chromatography, such as the aromatic polymer.

Example 2: Hydrodearylation of an Aromatic Chemical (with an Aromatic Polymer)

In Example 2, 300 g of an aromatic polymer, polystyrene (commercially available as Styrofoam from Dow), was dissolved in 6,000 g of an aromatic chemical. The properties of the aromatic chemical, prior to the addition of the polystyrene, are shown in Table 2. The aromatic chemical stream, with the addition of the aromatic polymer, was combined in a hydrodearylation unit with catalyst and hydrogen at reaction conditions of 350° C., a pressure of 80 bar, and a liquid hourly space velocity of 1.6. The same aromatic chemical stream, with the addition of the aromatic polymer, was combined in a hydrodearylation unit with catalyst and hydrogen at reaction conditions of 350° C., a pressure of 15 bar, and a liquid hourly space velocity of 1.6. The results of the hydrodearylation of the aromatic chemical stream, with the addition of the aromatic polymer, is shown in Table 3.

TABLE 3

| Property | Hydrodearylated Aromatic Chemical (with Aromatic Polymer) at 350° C., 80 bar, and LHSV of 1.6 | Hydrodearylated Aromatic Chemical (with Aromatic Polymer) at 350° C., 15 bar, and LHSV of 1.6 |
|---|---|---|
| Density (g/mL) | 0.9133 | 0.9236 |
| Initial Boiling Point (IBP) (° C.) | 68 | 71 |
| 10 wt. % Boiling Point (BP) (° C.) | 108 | 111 |
| 30 wt. % BP (° C.) | 161 | 162 |
| 50 wt. % BP (° C.) | 203 | 207 |
| 70 wt. % BP (° C.) | 240 | 243 |
| 90 wt. % BP (° C.) | 327 | 320 |
| Final Boiling Point (FBP) | 484 | 478 |
| Paraffins (wt. %) | 3.6 | 2.2 |
| Mono-Napthenes (wt. %) | 2.6 | 1.6 |
| Di-Napthenes (wt. %) | 0.7 | 0.4 |
| Mono Aromatics (wt. %) | 41.2 | 41.9 |
| Naptheno Mono Aromatics (wt. %) | 28.5 | 24.5 |
| Diaromatics (wt. %) | 14.2 | 20.5 |
| Naptheno Di Aromatics (wt. %) | 5.8 | 5.3 |
| Tri/Tetra Aromatics (wt. %) | 3.4 | 3.6 |
| Benzene, Toluene, Xylene (wt. %) | 26.8 | 27.9 |
| Non-GC Compatible Material (wt. %) | 0.1 | 1.7 |

As compared with Table 2, Table 3 shows that the amount of benzene, toluene, and xylene in the hydrodearylated aromatic chemicals, with the addition of the aromatic polymer, at 350° C., an LHSV of 1.6 h$^{-1}$, and varying pressures of 80 bar and 15 bar, is 26.8 wt. % and 27.9 wt. %, respectively. For the hydrodearylated aromatic chemical results at 80 bar, the gas chromatography detected 99.9 wt. % of the hydrodearylated aromatic chemical, as 0.1 wt. % of the hydrodearylated aromatic chemical was not gas chromatography compatible. The non-gas chromatography compatible material may be unconverted polystyrene or hydrodearylated polystyrene containing a small amount of large oligomers. Similarly, for the hydrodearylated aromatic chemical results at 15 bar, the gas chromatography detected 98.3 wt. % of the hydrodearylated aromatic chemical, as 1.7 wt. % of the hydrodearylated aromatic chemical was not gas chromatography compatible. The GC data in Table 3 has been normalized to 100%.

Comparative Example 2: Hydrodearylation of an Aromatic Chemical (without an Aromatic Polymer)

In Comparative Example 2, the aromatic chemicals of Example 2, without the addition of the aromatic polymer, were hydrodearylated at the same process conditions. The results are shown in Table 4.

TABLE 4

| Property | Hydrodearylated Aromatic Chemical (without Aromatic Polymer) at 350° C., 80 bar, and LHSV of 1.6 | Hydrodearylated Aromatic Chemical (without Aromatic Polymer) at 350° C., 15 bar, and LHSV of 1.6 |
| --- | --- | --- |
| Density (g/mL) | 0.9318 | 0.9478 |
| Initial Boiling Point (IBP) (° C.) | 83 | 80 |
| 10 wt. % Boiling Point (BP) (° C.) | 115 | 137 |
| 30 wt. % BP (° C.) | 171 | 174 |
| 50 wt. % BP (° C.) | 224 | 222 |
| 70 wt. % BP (° C.) | 256 | 254 |
| 90 wt. % BP (° C.) | 329 | 314 |
| Final Boiling Point (FBP) | 449 | 407 |
| Paraffins (wt. %) | 2.2 | 0.5 |
| Mono-Napthenes (wt. %) | 1.8 | 0.3 |
| Di-Napthenes (wt. %) | 1.6 | 0.1 |
| Mono Aromatics (wt. %) | 37.4 | 39.0 |
| Naptheno Mono Aromatics (wt. %) | 25.3 | 14.2 |
| Diaromatics (wt. %) | 20.8 | 34.0 |
| Naptheno Di Aromatics (wt. %) | 6.2 | 4.7 |
| Tri/Tetra Aromatics (wt. %) | 4.7 | 7.2 |
| Benzene, Toluene, Xylene (wt. %) | 20.3 | 21.1 |
| Non-GC Compatible Material (wt. %) | N/A | N/A |

As compared with Table 3, Table 4 shows that the amount of benzene, toluene, and xylene in the hydrodearylated aromatic chemicals, without the addition of the aromatic polymer, at 350° C., an light hourly space velocity of 1.6 $h^{-1}$, and varying pressures of 80 bar and 15 bar, is only 20.3 wt. % and 21.1 wt. %, respectively. Thus, the addition of the aromatic polymer to the aromatic chemical results in a marked increase, an increase greater than 30%, when hydrodearylating the aromatic chemical, evidencing the synergistic effect when hydrodearylating one or more aromatic-based polymers with one or more aromatic feed chemicals.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

One or more aspects of the present disclosure are described herein. A first aspect may include a process for the production of one or more of benzene, toluene, or mixed xylenes, the process comprising: combining one or more aromatic feed chemicals, one or more aromatic-based polymers, hydrodearylation catalyst, and hydrogen in a hydrodearylation unit to form a chemical product, wherein the one or more aromatic feed chemicals are chosen from one or more of $C_9+$ alkyl aromatics or alkyl-bridged non-condensed alkyl multi-aromatic compounds, wherein the alkyl-bridged non-condensed alkyl multi-aromatic compounds include at least two benzene rings connected by an alkyl bridge group having at least two carbons, and wherein the benzene rings are connected to different carbons of the alkyl bridge group; and passing the chemical product out of the hydrodearylation unit, wherein the chemical product comprises one or more of benzene, toluene, and mixed xylenes.

A second aspect includes the first aspect, wherein the one or more aromatic feed chemicals and one or more aromatic-based polymers are mixed in a mixing unit and passed to the hydrodearylation unit to be combined with the hydrodearylation catalyst.

A third aspect includes the first aspect, wherein the mixing unit operates at a temperature of less than or equal to 300° C. and a pressure of from 1 bar to 200 bars.

A fourth aspect includes the first aspect, wherein the weight ratio of the one or more aromatic-based polymers to the one or more aromatic feed chemicals is at least 1:1000.

A fifth aspect includes the first aspect, wherein the weight ratio of the one or more aromatic-based polymers to the one or more aromatic feed chemicals is less than or equal to 1:1.

A sixth aspect includes the first aspect, wherein the amount of aromatic-based polymer mixed with the aromatic feed chemicals is at least 90% of the amount of aromatic-based polymer needed to achieve maximum saturation.

A seventh aspect includes the first aspect, wherein the aromatic-based polymer comprises one or more of polystyrene, polyphenylenes, poly(p-xylenes), poly(phenylenevinylenes), polybenzyls, or combinations thereof.

An eighth aspect includes the first aspect, wherein the aromatic-based polymer comprises polystyrene.

A ninth aspect includes the first aspect, wherein the hydrodearylation catalyst is positioned as a fixed bed in the hydrodearylation unit.

A tenth aspect includes the first aspect, wherein the hydrodearylation catalyst comprises: a support comprised of one or more of silica, alumina, titania and combinations thereof; and an acidic component comprised of one or more of amorphous silica-alumina, zeolite, and combinations thereof.

An eleventh aspect includes the tenth aspect, wherein the hydrodearylation catalyst further comprises: an IUPAC Group 8-10 metal comprised of one or more of iron, cobalt, and nickel, and combinations thereof; and an IUPAC Group 6 metal comprising one or more of molybdenum and tungsten, and combinations thereof.

A twelfth aspect includes the eleventh aspect, wherein the IUPAC Group 8-10 metal comprises 2 to 20 percent by weight of the catalyst; and the IUPAC Group 6 metal comprises 1 to 25 percent by weight of the catalyst.

A thirteenth aspect includes the first aspect, wherein the hydrodearylation catalyst is positioned as an ebullated bed or a moving bed in the hydrodearylation unit.

A fourteenth aspect includes the first aspect, wherein the hydrodearylation unit is operated at a temperature of from 200° C. to 450° C.

A fifteenth aspect includes the first aspect, further comprising passing the chemical product to a downstream paraxylene recovery system.

A sixteenth aspect includes the first aspect, wherein the aromatic feed chemicals are products of an aromatics complex.

A seventeenth aspect includes the first aspect, wherein the one or more aromatic feed chemicals comprise $C_{11}+$ alkyl aromatic compounds.

A eighteenth aspect includes the seventeenth aspect, wherein the one or more aromatic feed chemicals are a heavy fraction of a feed stream comprising $C_{9+}$ alkyl aromatics.

An nineteenth aspect includes the first aspect, wherein a first portion of an initial feed stream comprising $C_9+$ alkyl aromatics is passed to a mixing unit and a second portion of the initial feed stream comprising $C_9+$ alkyl aromatics is passed to a separation unit.

A twentieth aspect may include a system for the production of one or more of benzene, toluene, or mixed xylenes, the system comprising: a mixing unit; a hydrodearylation unit comprising hydrodearylation catalyst and hydrogen; an aromatic feed stream in fluid communication with a mixing unit; an aromatic-based polymer stream in fluid communication with the mixing unit; a mixing unit effluent stream in fluid communication between the mixing unit and the hydrodearylation unit; a chemical product stream in fluid communication with the hydrodearylation unit, the chemical product stream comprising one or more of benzene, toluene, or mixed xylenes.

A twenty-first aspect includes the twentieth aspect, further comprising a separation unit, the separation unit comprising: the aromatic feed in fluid communication with the separation unit; a light aromatic chemical in fluid communication with the separation unit; and a heavy aromatic chemical in fluid communication between the separation unit and the mixing unit.

What is claimed is:

1. A process for the production of one or more of benzene, toluene, or mixed xylenes, the process comprising:
   providing an aromatic feed chemical stream comprising one or more aromatic feed chemicals;
   mixing at least a portion of the aromatic feed chemical stream with one or more aromatic-based polymers in a mixing unit comprising a mixing vessel and a mixer, wherein:
      the one or more aromatic feed chemicals are chosen from one or more of $C_{9+}$ alkyl aromatics or alkyl-bridged non-condensed alkyl multi-aromatic compounds,
      the alkyl-bridged non-condensed alkyl multi-aromatic compounds include at least two benzene rings connected by an alkyl bridge group having at least two carbons,
      the benzene rings are connected to different carbons of the alkyl bridge group,
      the one or more aromatic feed chemicals are liquid,
      the one or more aromatic-based polymers are solids,
      the aromatic feed chemical stream comprises less than 1 weight percent BTX, and
      the mixing causes at least a portion of the aromatic-based polymers to dissolve into the one or more aromatic feed chemicals to produce a mixing unit effluent stream;
   passing the mixing unit effluent stream to a hydrodearylation unit downstream of the mixing unit;
   combining the mixing unit effluent stream with a hydrodearylation catalyst and hydrogen in the hydrodearylation unit, where the combining produces a chemical product; and
   passing the chemical product out of the hydrodearylation unit, wherein the chemical product comprises one or more of benzene, toluene, and mixed xylenes.

2. The process of claim 1, wherein the mixing unit operates at a temperature of less than or equal to 300° C. and a pressure of from 1 bar to 200 bars.

3. The process of claim 1, wherein the weight ratio of the one or more aromatic-based polymers to the one or more aromatic feed chemicals is at least 1:1000 and less than or equal to 1:1.

4. The process of claim 1, wherein the amount of aromatic-based polymer mixed with the aromatic feed chemicals is at least 90% of the amount of aromatic-based polymer needed to achieve maximum saturation.

5. The process of claim 1, wherein the aromatic-based polymer comprises one or more of polystyrene, polyphenylenes, poly(p-xylenes), poly(phenylenevinylenes), polybenzyls, or combinations thereof.

6. The process of claim 1, wherein the aromatic-based polymer comprises polystyrene.

7. The process of claim 1, wherein the hydrodearylation catalyst is positioned as a fixed bed in the hydrodearylation unit.

8. The process of claim 1, wherein the hydrodearylation catalyst comprises:
   a support comprised of one or more of silica, alumina, titania and combinations thereof;
   an acidic component comprised of one or more of amorphous silica-alumina, zeolite, and combinations thereof;
   an IUPAC Group 8-10 metal comprised of one or more of iron, cobalt, and nickel, and combinations thereof; and
   an IUPAC Group 6 metal comprising one or more of molybdenum and tungsten, and combinations thereof.

9. The process of claim 8, wherein:
   the IUPAC Group 8-10 metal comprises 2 to 20 percent be weight of the catalyst; and
   the IUPAC Group 6 metal comprises 1 to 25 percent by weight of the catalyst.

10. The process of claim 1, wherein the hydrodearylation unit is operated at a temperature of from 200° C. to 450° C.

11. The process of claim 1, further comprising passing the chemical product to a downstream para-xylene recovery system.

12. The process of claim 1, wherein the one or more aromatic feed chemicals are products of an aromatics complex.

13. The process of claim 1, wherein the one or more aromatic feed chemicals comprise $C_{11}+$ alkyl aromatic compounds.

14. The process of claim 13, wherein the one or more aromatic feed chemicals are a heavy fraction of a feed stream comprising $C_9+$ alkyl aromatics.

15. The process of claim 1, further comprising:
passing a first portion of the aromatic feed chemical stream to the mixing unit; and
passing a second portion of the aromatic feed chemical stream to a separation unit.

16. The process of claim 1, further comprising:
separating crude oil in an atmospheric distillation unit to produce naphtha;
passing the naphtha to a hydrotreating unit operable to hydrotreat the naphtha to produce hydrotreated naphtha;
passing the hydrotreated naphtha to a naphtha reforming unit operable to reform the hydrotreated naphtha to produce a reformate; and
passing the reformate to an aromatic complex operable to separate the reformate to produce one or more C9– aromatics, a gasoline pool stream, and the aromatic feed chemical stream comprising the one or more aromatic feed chemicals.

17. The process of claim 16, further comprising passing the aromatic feed chemical stream to the mixing unit.

18. The process of claim 1, further comprising:
separating recycled aromatic feed chemicals from the chemical product; and
combining the recycled aromatic feed chemicals with the one or more aromatic feed chemicals upstream of the hydrodearylation unit to form a combined aromatic chemical feed.

19. A process for the production of one or more of benzene, toluene, or mixed xylenes, the process comprising:
providing an aromatic feed chemical stream comprising one or more aromatic feed chemicals;
passing a first portion of the aromatic feed chemical stream to a first mixing unit;
passing a second portion of the aromatic feed chemical stream to a separation unit;
mixing the first portion of the aromatic feed chemical stream and one or more aromatic-based polymers in the first mixing unit comprising a mixing vessel and a mixer, wherein:
the one or more aromatic feed chemicals are chosen from one or more of $C_9+$ alkyl aromatics or alkyl-bridged non-condensed alkyl multi-aromatic compounds,
the alkyl-bridged non-condensed alkyl multi-aromatic compounds include at least two benzene rings connected by an alkyl bridge group having at least two carbons,
the benzene rings are connected to different carbons of the alkyl bridge group,
the one or more aromatic feed chemicals are liquid,
the one or more aromatic-based polymers are solids, and
the mixing causes at least a portion of the aromatic-based polymers to dissolve into the one or more aromatic feed chemicals to produce a first mixing unit effluent stream;
passing the first mixing unit effluent stream to a hydrodearylation unit downstream of the mixing unit;
combining the first mixing unit effluent stream with a hydrodearylation catalyst and hydrogen in the hydrodearylation unit, where the combining produces a chemical product; and
passing the chemical product out of the hydrodearylation unit, wherein the chemical product comprises one or more of benzene, toluene, and mixed xylenes.

20. The process of claim 19, further comprising:
separating the second portion of the aromatic feed chemical stream to produce a light aromatic chemical stream and a heavy aromatic chemical stream;
passing the heavy aromatic chemical stream to a second mixing unit;
mixing the heavy aromatic chemical stream with the one or more aromatic-based polymers in the second mixing unit to produce a second mixing unit effluent; and
passing the second mixing unit effluent to the hydrodearylation unit.

* * * * *